US00PP10320P

United States Patent [19]

Kientzler

[11] Patent Number: Plant 10,320

[45] Date of Patent: Apr. 7, 1998

[54] NEW GUINEA IMPATIENS PLANT NAMED 'TARAWA'

[75] Inventor: Ludwig Kientzler, Gensingen, Germany

[73] Assignee: Paul Ecke Ranch, Inc., Encinitas, Calif.

[21] Appl. No.: 775,972

[22] Filed: Jan. 3, 1997

[51] Int. Cl.[6] ..... A01H 5/00

[52] U.S. Cl. ..... Plt./87.6

[58] Field of Search ..... Plt./87.6

*Primary Examiner*—James R. Feyrer
*Attorney, Agent, or Firm*—C. A. Whealy

[57] ABSTRACT

A new and distinct cultivar of New Guinea Impatiens plant named 'Tarawa', characterized by its flat and rounded red-colored flowers; freely flowering habit; outwardly spreading, rounded and mounding growth habit; and dark green, slightly glossy, non-variegated foliage.

1 Drawing Sheet

The present invention relates to a new and distinct cultivar of New Guinea Impatiens plant, botanically known as *Impatiens hawkeri*, known by the name 'Kirawa', and hereinafter referred to by the cultivar name 'Tarawa'.

The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made bythe inventor of a proprietary seedling selection identified as R556 as the male, or pollen parent, with the proprietary seedling selection identified as O419 as the female, or seed patent. The cultivar Tarawa was discovered and selected by the inventot as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction.

The following traits have been repeatedly observed and are determined to be the unique characteristics of 'Tarawa'. These characteristics in combination distinguish 'Tarawa' as a new and distinct cultivar:

1. Flat and rounded red-colored flowers.
2. Freely flowering habit.
3. Outwardly spreading, rounded and mounding growth habit.
4. Dark green, slightly glossy, non-variegated foliage.

The new New Guinea Impatiens is similar in flower color to the New Guinea Impatiens cultivar 'Lanai' (disclosed in U.S. Plant Pat. No. 8,397). However in side-by-side comparisons in Encinitas, Calif., under commercial practice, plants of the New Guinea Impatiens differed from plants of the cultivar 'Lanai' in the following characteristics:

1. Plants of the new New Guinea Impatiens are more outwardly spreading and rounded than plants of the cultivar 'Lanai'.
2. Plants of the new Guinea Impatiens have dark red stems whereas plants of the cultivar 'Lanai' have green stems with red streaks.
3. Leaves of plants of the new Guinea Impatiens are not as glossy as leaves of plants of the cultivar 'Lanai'.
4. Lower surfaces of mature leaves of plants of the new Guinea Impatiens are grayed red in color whereas lower surfaces of mature leaves of the cultivar 'Lanai' are light green.
5. Plants of the new New Guinea Impatiens are more freely flowering than plants of the cultivar 'Lanai'.

6. Flowers of plants of the new New Guinea Impatiens are larger, flatter and more rounded than flowers of plants of the cultivar 'Lanai'.
7. Peduncles of plants of the new New Guinea Impatiens are longer than peduncles of plants of the cultivar 'Lanai'.

A detailed comparison of plants of the new New Guinea Impatiens and the cultivar 'Lanai' appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical plant of 'Tarawa'.

The second photograph comprises a close-up view of typical flowers and upper (left) and lower (right) surfaces of leaves of the varieties 'Lanai' (top) and 'Tarawa' (bottom).

Flower and foliage colors in the photographs may differ from the actual colors due to light reflectance.

The cultivar 'Tarawa' has not been observed under all possible environmental conditions. The phenotpe may vary somewhat with variations in environment such as temperature and light intensity, without, however, any variance in genotype. The following observations, measurements and comparisons describe plants grown 10-cm pots in Encinitas, Calif., under commercial practice in a fiberglass-covered greenhouse with day temperatures ranging from 23 to 29 C. and night temperatures ranging from 16 to 18 C. and light levels averaging 3,000 footcandles.

In the following description, color references are made to The Royal Horticultural Society Colour Chart except where general terms of ordinary dictionary significance are used.

Classification:

*Botanical.*—*Impatiens hawkeri* 'Tarawa'.

*Commercial.*—New Guinea Impatiens cv. 'Tarawa'.

Parentage:

*Male parent.*—Proprietary seedling selection R556.

*Female parent.*—Proprietary seedling selection O419.

Propagation:

*Type cutting.*—Terminal cuttings.

*Time to initiate roots.*—About 15 days with 21 C. soil temperature.

Plant description:

*Plant form.*—Outwardly spreading, rounded, mounding.

*Growth habit.*—Moderately vigorous. Moderate branching. Suitable for 10 to 25-cm containers.

*Plant size.*—Height: About 26 cm. Width or spread: About 28 cm.

*Lateral branches.*—Quantity: About five. Size: Length: About 12 cm. Diameter: About 1.1 cm. Internode length: 3.5 to 4 cm. Color: Darker than 59A.

*Foliage description.*—Leaves simple, generally symmetrical, abundant, opposite or in whorls of three, horizontal to plant and flat in aspect. Size, largest leaves: Length: 11 to 11.5 cm. Width: About 4.5 cm. Shape: Ovate with acuminate apex, attenuate base and ciliate margin. Texture: Smooth, slightly glossy. Color: Young foliage, upper surface: Darker than 147A. Young foliage, lower surface: 59A. Fully expanded foliage, upper surface: 147A. Fully expanded foliage, lower surface: Grayer than 59C. Venation, upper surface: 59B. Venation, lower surface: 59A. Petiole: Size: Length: 2.5 to 3.5 cm. Diameter: About 3.5 mm. Color: 60A.

Flower description:

*Flower type and habit.*—Red-colored flowers. Freely and continuously flowering. Flowers arise from leaf axils. Usually eight to ten flowers per lateral branch. Flowers positioned at or just above the foliage and face outward. Flowers flat and rounded. Flowers persistent.

*Flowering season.*—Year-round under greenhouse conditions. In the garden, flowering is continuous from spring until fall.

*Flower size.*—Length: About 6 cm. Width: About 6 cm. Depth: About 4 mm.

*Flower buds.*—Size: Length: About 2.5 cm. Diameter: About 1.4 cm. Shape: Ovoid. Color: 44A.

*Petals.*—Quantity: Five Size (largest petals): Length: Top petal: About 3 cm. Middle petals: About 3.2 cm. Bottom petals: About 4 cm. Width: Top petal: About 5 cm. Middle petals: About 3.5 cm. Bottom petals: About 4.2 cm. Shape: Cordate with emarginate apex, cuneate or obtuse base and entire margin. Texture: Velvety, smooth. Color: When opening, upper surface: Iridescent, slightly brighter than 44A. When opening, lower surface: Iridescent, 44B. Fully opened, upper surface: Iridescent, 43A, with 57B at base. Top petal has center streaking of 47B/47C. Fully opened, lower surface: Iridescent, 44B. Fading to: Color does not fade.

*Spur.*—Length: About 5.2 cm. Shape: Narrow and curved. Color: Proximal: 60A. Distal tip: 59A.

*Peduncles.*—Length: About 5.4 cm. Angle: Outward. Strength: Strong. Color: 60A

*Reproductive organs.*—Androecium: Stamen number: Five, anthers fused, filaments free. Anther shape: Obovate. Anther size: 6 by 4 mm. Anther color: 15C. Amount of pollen: Moderate. Pollen color: Creamy white. Gynoecium: Five-loculate fused. Gynoecium length: About 5 mm. Gynoecium color: 59A.

Disease resistance: Under commercial conditions, resistance nor susceptibility to pathogens has not been observed.

Seed development: Seed production is not usually observed.

CHART A

| CHARACTERISTIC | 'TARAWA' | 'LANAI' |
|---|---|---|
| GROWTH HABIT | Outwardly spreading, rounded, and mounding | Upright, open, mounding |
| PLANT HEIGHT | About 26 cm | About 28 cm |
| PLANT WIDTH | About 28 cm | About 26 cm |
| NUMBER OF LATERAL BRANCHES | About 5 | About 7 |
| LATERAL BRANCH LENGTH | About 12 cm | About 13 cm |
| LATERAL BRANCH DIAMETER | About 1.1 cm | About 8 mm |
| INTERNODE LENGTH | 3.5 to 4 cm | About 6 cm |
| STEM COLOR | Darker than 59A | 147C with 59C streaks |
| LEAF LENGTH | 11 to 11.5 cm | About 10 cm |
| LEAF TEXTURE | Smooth, slightly glossy | Smooth, glossy |
| LEAF COLOR, YOUNG, UPPER SURFACE | Darker than 147A | 137A |
| LEAF COLOR, YOUNG, LOWER SURFACE | 59A | 137C |
| LEAF COLOR, MATURE, UPPER SURFACE | 147A | 147A |
| LEAF COLOR, MATURE, LOWER SURFACE | Grayer than 59C | 147C |
| LEAF VENATION COLOR, UPPER SURFACE | 59B | 63C/63D |
| LEAF VENATION COLOR, LOWER SURFACE | 59A | 63B |
| PETIOLE COLOR | 60A | 50B |
| NUMBER OF FLOWERS | 8 to 10 | 7 to 8 |
| FLOWER ASPECT | Flat | Cupped |
| FLOWER SHAPE | Rounded | Rectangular |
| FLOWER LENGTH | About 6 cm | About 5 cm |
| FLOWER WIDTH | About 6 cm | About 5.2 cm |
| FLOWER DEPTH | About 4 mm | About 5 mm |
| PEDUNCLE LENGTH | About 5.4 cm | About 4 cm |
| PEDUNCLE ANGLE | Outward | Most erect and some outward |
| PEDUNCLE COLOR | 60A | 59C |
| FLOWER BUD COLOR | 44A | 46B |

It is claimed:

1. A new and distinct cultivar of New Guinea Impatiens plant named 'Tarawa', as illustrated and described.

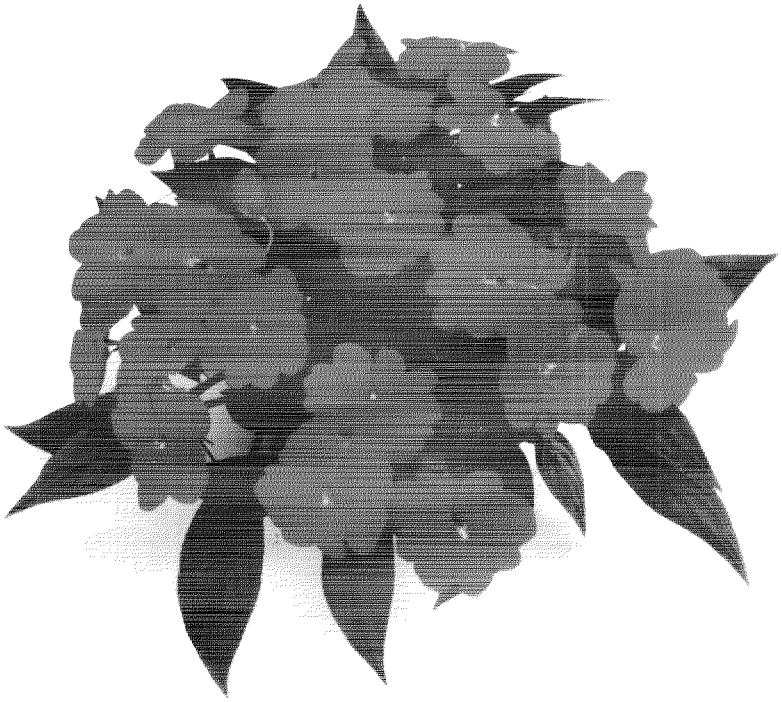
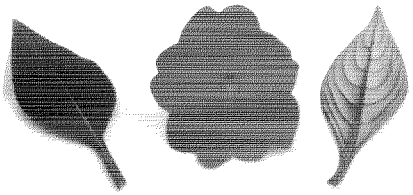
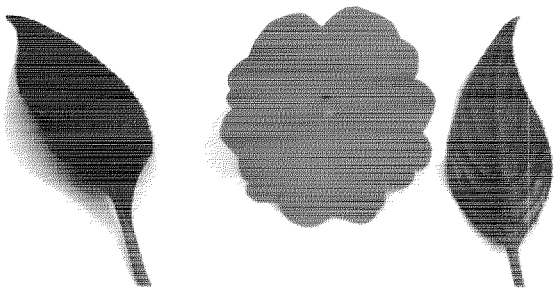

* * * * *